United States Patent [19]

Simmons et al.

[11] 4,090,866
[45] May 23, 1978

[54] PROCESS FOR THE SELECTIVE CONTROL OF TALL FESCUE IN TURF

[75] Inventors: James Almy Simmons; George Edson Wood; Paul Leroy Jacquemin, all of Marysville, Ohio

[73] Assignee: O. M. Scott & Sons Company, New York, N.Y.

[21] Appl. No.: 777,136

[22] Filed: Mar. 14, 1977

[51] Int. Cl.² ............................................. A01N 9/24
[52] U.S. Cl. ..................................................... 71/108
[58] Field of Search ................................. 71/108, 116

[56] References Cited

U.S. PATENT DOCUMENTS 3,954,442  5/1976  Becker et al. ........................... 71/108

Primary Examiner—Catherine L. Mills
Attorney, Agent, or Firm—James B. Raden; Harold J. Holt

[57] ABSTRACT

A process for the selective control of tall fescue and perennial ryegrass in Kentucky bluegrass, fine fescue or bentgrass turf comprising treating said turf with a compound selected from the group consisting of (a) 4-(4'-chlorophenoxy)-phenoxy-d-propionic-isobutylester and (b) methyl 2-[4-(2,4-dichlorophenoxy)-phenoxy]-propanoate, in an amount effective to kill said tall fescue or perennial ryegrass but insufficient to damage said turf.

8 Claims, No Drawings

PROCESS FOR THE SELECTIVE CONTROL OF TALL FESCUE IN TURF

This invention relates to a process for the selective control of tall fescue and perennial ryegrass in Kentucky bluegrass, fine fescue or bentgrass turf. Tall fescue (*Festuca arundinacea*) is a widely grown perennial introduced from Europe a number of years ago. It has a deeply rooted and strongly leafed growth habit. The blades are flat, wide and where the plant is growing as single isolates in a lawn or pasture, the blade growth can parallel the ground level for a short distance from the crown. Tall fescue does not develop rhizomes or stolons. However, new tillers do arise around the outer edge of the crown area which contribute to a spreading-like quality to individual plants.

Tall fescue is a widely adapted plant and has been found useful in both agriculture and the turfgrass industry. It performs well under certain athletic field conditions, low lawn maintenance situations in the north and west where fine leaf texture is not necessary, as a seeded lawn grass in the upper southern states where bermudagrass is the predominant lawn species and on roadside right-of-ways.

Tall fescue must be seeded at heavy seeding rates to obtain a stand of upright growing and a reasonably dense plant stand. Such a stand performs well on a low fertilizer regime, has superior tolerance to hot weather, and droughty situations in comparison to most other grasses used for turfgrass purposes.

The growth characteristics that can make tall fescue a desirable plant can also result in its becoming the most serious weed problem of the homeowner or professional turfgrass manager. Isolated coarse clumping plants of tall fescue in a sward of Kentucky bluegrass, fine fescues, bentgrasses, etc., is a most unsightly turfgrass planting. Such isolate plants can occur from the following situations: (1) new housing starts on farm land planted to tall fescue at one time, (2) tall fescue used at the wrong seeding rate and percentages in seed mixtures, and (3) a stand of tall fescue that has been allowed to thin for one or more reasons and (4) as a possible seed mixture contaminant.

In spite of considerable effort toward the development of a herbicide which will selectively control tall fescue in turf grass, no such herbicide has yet been found. As a result, tall fescue has been controlled by such measures as (1) physical removal by digging it out of the stand, (2) use of a nonselective herbicide, or (3) replacing the lawn. These measures, especially the first two, are very unsatisfactory if there are more than a few widely scattered plants in the lawn. Lawn replacement is obviously very costly. The digging procedure must be deep enough to insure the removal of any crown tissue that could result in regrowth. The chemical method must include provisions for follow-up treatments, as tall fescue is a most difficult plant to kill. This treatment will kill all desirable grasses exposed to the chemical. A damaged lawn either caused by digging or chemical action must be reseeded to restore the appearance of the stand. Where the plant has been mechanically removed, soil must be replaced before seeding to retain a smooth soil surface. The soil in chemical treated areas must be mechanically disturbed enough to provide a good seedbed. These seedings must be kept moist long enough to germinate the seed if a new grass stand is to be produced in a short period of time. As a result, most owners regardless of how much they dislike tall fescue, choose to live with a contaminated lawn rather than attempt any of the available methods of control.

German published Patent Applications Nos. 2,223,894 and 2,427,270 to Hoechst disclose the use of 4-phenoxy-α-phenoxy propionic acid esters as selective herbicides for the control of weedy grasses in crop plants. However, such compounds have been reported to be useful for the control only of annual weedy grasses. Perennial weed grasses are normally much more difficult to control. Moreover, even with respect to annual grasses, the herbicides have been reported to be ineffective for control of *Poa Annua* or annual bluegrass.

It is accordingly a primary object of the present invention to provide an effective process for the selective control of tall fescue in established turf.

It is an additional object of the invention to provide a process which, in addition to tall fescue, is also effective for the selective control of perennial ryegrass in established turf.

It has been discovered that the compounds methyl 2-[4-(2,4-dichlorophenoxy)-phenoxy]propanoate and 4-(4'-chlorophenoxy)-phenoxy-d-propionic-isobutylester are effective for the selective control of both tall fescue and perennial ryegrass in established turfs of Kentucky bluegrass, fine fescue and bentgrass. Although perennial ryegrass is not as severe a problem as tall fescue, individual growing plants can represent a weed problem for which there has been no effective selective control in turf. The compounds of the invention have been found to kill tall fescue and perennial ryegrass without causing serious adverse response in desirable turfs. This discovery is believed particularly surprising, not only because of the vast numbers of compounds which have been tested and proven unsuccessful for this purpose, but also because the compounds themselves have been reported to be ineffective against perennial grass weeds. Insofar as is known, these are the first compounds which have been found to exhibit effective selective control of tall fescue in Kentucky bluegrass.

The following examples illustrate the practice of the invention.

EXAMPLE 1

Spray formulations were prepared by mixing the herbicidal compounds (36% active emulsifiable concentrate) of the invention with water to produce a formulation which delivered 44 gallons of spray per acre. The herbicidal compound in the two formulations was (A) 4-(4'-chlorophenoxy)-phenoxy-d-propionic-isobutylester and (B) methyl 2-[4-(2,4-dichlorophenoxy)-phenoxy]-propanoate.

A series of field tests were conducted with these formulations. The testing site was a series of turfgrass strips that had been previously established from sod. The turfgrasses included Penncross bentgrass, Merion Kentucky bluegrass, K-31 tall fescue, Biljart hard fescue, Pennfine perennial ryegrass and *Poa annua*. The grasses were laid parallel to each other in eighteen inch sod strips 200 feet in length. Six of these grass blocks were planted. Applications were made with the formulations across the grass in plot widths up to two feet wide and nine feet long. Replications were obtained by repeating the treatments on the turfgrass strips.

Formulations A and B were tested in this Example to determine whether they were root active. After application of the sprays, they were immediately rinsed from the foliage with sufficient water to insure that the chemical was moved to the soil. Table I shows the percent of the respective weed coverage remaining 29 days after application and the average percent control of two tests (T1 and T2). Lbs./A is pounds of active ingredient per acre used in the respective tests.

TABLE I

| | | ROOT ACTIVITY | | | | | |
|---|---|---|---|---|---|---|---|
| | | Tall Fescue (%) | | | Perennial Rye (%) | | |
| Formulation | Lbs./A | T1 | T2 | % Control | T1 | T2 | % Control |
| A | 4 | 100 | 100 | 0 | 85 | 100 | 7.5 |
| | 8 | 90 | 100 | 5 | 70 | 100 | 15 |
| | 16 | 20 | 40 | 70 | 20 | 30 | 75 |
| B | 2 | 97 | 100 | 3 | 90 | 100 | 5 |
| | 4 | 75 | 95 | 15 | 15 | 50 | 67 |
| | 8 | 10 | 80 | 55 | 10 | 30 | 80 |

It wil be seen that formulation A gave 70% control of tall fescue and 75% control of perennial rye through root activity at 16 lbs./acre. Formulation B gave 55% and 80% control, respectively, also through root activity, at 8 lbs./acre.

Table II shows the tolerance of the various turf grasses tested in this Example.

TABLE II

| | | Tolerance - Soil Application | | | | | |
|---|---|---|---|---|---|---|---|
| | | Discoloration* | | | % Thinning | | |
| Formulation | Lbs./Acre | Bentgrass | Bluegrass | Hard Fescue | Bentgrass | Bluegrass | Hard Fescue |
| A | 4 | 0 | 0 | 0 | 0 | 0 | 0 |
| | 8 | 0 | 0 | 0 | 0 | 0 | 0 |
| | 16 | 0.5 | 0.5 | 0 | 2.5 | 0 | 5 |
| B | 2 | 0 | 0 | 0 | 0 | 0 | 2.5 |
| | 4 | 0.5 | 0 | 0.5 | 0 | 0 | 0 |
| | 8 | 1.5 | 0.5 | 0.5 | 0 | 5 | 7.5 |

*10 = brown; 0 = no browning.

Discoloration of desirable turf was accordingly slight, although some thinning is apparent at the higher application rates.

EXAMPLE 2

In this example, the same spray formulations described in Example 1 were applied as there set forth, except that the sprays were allowed to remain on the foliage for at least 24 hours following application to test their foliar activity. The results are set forth in Table III.

TABLE III

| | | Foliar Activity | | | | | |
|---|---|---|---|---|---|---|---|
| | | Tall Fescue (%) | | | Perennial Rye (%) | | |
| Formulation | Lbs./A. | T1 | T2 | % Control | T1 | T2 | % Control |
| A | 4 | 100 | 95 | 2 | 70 | 85 | 22 |
| | 8 | 60 | 70 | 35 | 5 | 30 | 82 |
| | 16 | 20 | 20 | 80 | 5 | 5 | 95 |
| B | 2 | 95 | 30 | 38 | 40 | 40 | 60 |
| | 4 | 50 | 60 | 45 | 5 | 15 | 90 |
| | 8 | 30 | 70 | 50 | 0 | 5 | 97 |

Table Iv shows the tolerance of the various turf grasses tested in this example.

TABLE IV

| | | Tolerance - Foliar Application | | | | | |
|---|---|---|---|---|---|---|---|
| | | Discoloration | | | % Thinning | | |
| Formulation | Lbs./Acre | Bentgrass | Bluegrass | Hard Fescue | Bentgrass | Bluegrass | Hard Fescue |
| A | 4 | 1.0 | 0.5 | 0 | 0 | 0 | 0 |
| | 8 | 1.5 | 1.5 | 0 | 5 | 0 | 0 |
| | 16 | 1.0 | 1.0 | 0 | 0 | 0 | 0 |
| B | 2 | 1.5 | 1.0 | 0 | 0 | 2.5 | 0 |
| | 4 | 1.5 | 0 | 0.5 | 5 | 0 | 0 |
| | 8 | 2.5 | 0 | 0 | 25 | 2.5 | 0 |

EXAMPLE 3

A granular formulation of 4-(4'-chlorophenoxy)-phenoxy-d-propionic-isobutylester was prepared by mixing the compound with a vermiculite carrier to produce an 8.5% by weight of the active ingredient granular formulation. The formulations were applied to the same turfgrass strips described in Example 1, but were applied with a granular spreader. Results were measured thirty-three days after treatment. Results are set forth in Table V.

TABLE V

| | Activity - Granular Application | | | | | |
|---|---|---|---|---|---|---|
| | Tall Fescue (%) | | | Perennial Rye (%) | | |
| Lbs./A | T1 | T2 | % Control | T1 | T2 | % Control |
| 4 | 100 | 100 | 0 | 100 | 100 | 0 |
| 8 | 20 | 20 | 80 | 50 | 80 | 35 |
| 16 | 5 | 10 | 92 | 25 | 5 | 85 |

Tolerance at 4, 8 and 16 lbs./acre by Merion Kentucky bluegrass, Penncross, bentgrass and Biljart hard fescue was excellent. No measurable discoloration or thinning occurred for all three turfgrasses at all rates tested.

EXAMPLE 4

These tests were designed to measure the control of tall fescue with both liquid and granular formulations on a Kentucky bluegrass lawn site contaminated with the problem grass. Individual plots were 4 feet × 8 feet and each treatment was repeated three times. In the following tests, compound A was 4-(4'-chlorophenoxy)-phenoxy-d-propionic-isobutylester, while compound B was methyl 2-[4-(2,4-dichloro-phenoxy)-phenoxy]-propanoate. Compound A granular formulation was applied at 4, 8 and 16 lbs./A and the liquid form at 4 and 8 lbs./A. Compound B as a granular formulation was applied at 2, 4 and 8 lbs./A and at 2 and 4 lbs./A as a liquid treatment. Granulars were applied on dew wet foliage. The liquid formulation was prepared as set forth in Example 1, while the granular formulation was prepared as set forth in Example 3, except that the granular formulation containing Compound B was a 4.59% formulation. The results of three replications of the granular wet applications and the liquid spray foliage applications are set forth in Table VI. The "check" results are untreated plots.

TABLE VI

| | | Tall Fescue (%) | | | | % Thinning of |
|---|---|---|---|---|---|---|
| | Lbs./A. | T1 | T2 | T3 | % Control | Blue Grass |
| Granular | 4 | 15 | 15 | 5 | 37 | 0 |
| Compound | 8 | 2 | 10 | 7 | 66 | 0 |
| A | 16 | 1 | 1 | 2 | 93 | 0 |
| Spray | 4 | 12 | 10 | 3 | 55 | 0 |
| Compound | 8 | 5 | 5 | 5 | 73 | 0 |
| A | | | | | | |
| Granular | 2 | 15 | 15 | 5 | 37 | 0 |
| Compound | 4 | 5 | 20 | 5 | 39 | |

TABLE VI-continued

|  | Lbs./A. | Tall Fescue (%) T1 | T2 | T3 | % Control | % Thinning of Blue Grass |
|---|---|---|---|---|---|---|
| B | 8 | 2 | 5 | 2 | 84 | 0 |
| Spray | 2 | 7 | 10 | 3 | 62 | 0 |
| Compound B | 4 | 5 | 5 | 4 | 73 | 0 |
| Check |  | 25 | 20 | 10 |  | 0 |

The rate at which the herbicide is used will depend on the particular compound, the type of formulation in which it is incorporated and the characteristics of the area to which it is applied. Single application rates of from 2 to 24 pounds of active ingredient per acre effectively control both tall fescue and perennial ryegrass with minimal or no turf damage. Repeat applications may be used at rates below the single application rate. Preferably the rate of application will vary from 4 to 20 pounds, with a preferred rate for 4-(4'-chlorophenoxy)-phenoxy-d-propionic-isobutylester being from 8 to 20 pounds per acre while the preferred rate for methyl 2-[4-(2,4-dichloro-phenoxy)-phenoxy]propanoate is from 4 to 12 pounds per acre.

The compounds of the invention may be prepared by known methods, as for example, by processes disclosed in German published patent applications Nos. 1,668,896 and 2,223,894. As shown in the examples, the compounds can be formulated as a liquid and applied as a spray or drench, or formulated as a granule or dust by placing on a dry carrier. Appropriate dry carriers include vermiculite, processed organic refuse, rice hulls, attapulgite clay, corn cob and fertilizer. Other carriers are described in "Handbook of Dust Diluents and Carriers" (2nd Ed.), 1955. U.S. Pat. Nos. 3,076,699 and 3,083,089 disclose methods for making granular formulations which may be used with the compounds of the present invention. For example, in those cases in which the compounds are supplied as solids at room temperature they may be dissolved in an appropriate solvent and adhered to a carrier in the manner disclosed in U.S. Pat. No. 3,083,089. Or particles of the compound may be adhered to a carrier with a suitable sticking agent as described in U.S. Pat. No. 3,076,699. In those cases in which the compounds are supplied as liquids, they can be similarly absorbed on exfoliated vermiculite as described in the foregoing patents.

Diluents, stabilizers, sticking agents, solvents, plant nutrients, other herbicides, flow enhancing agents, adhesives, dyes, and other adjuvants may also be employed in formulations in which the compounds of the present invention are incorporated. The above mentioned and other adjuvants which may be employed are described in "Weed Control" (2nd Ed.), Robbins et al, McGraw-Hill Book Company, Inc., New York, N.Y., 1952; and in U.S. Pat. No. 3,231,363, issued Jan. 25, 1966, to Victor A. Renner for Process For Making Foamed Urea-Formaldehyde Fertilizer, and U.S. Pat. No. 3,705,794, issued Dec. 12, 1972 for Foamed Fertilizers and Combination Products which disclose various combination products in which the compounds disclosed herein may be incorporated and method of preparing such formulation.

We claim:

1. A process for the selective control of tall fescue and perennial ryegrass in Kentucky bluegrass, fine fescue or bentgrass turf comprising treating said turf with a compound selected form the group consisting of (a) 4-(4'-chlorophenoxy)-phenoxy-d-propionic-isobutylester and (b) methyl 2-[4-(2,4-dichlorophenoxy)-phenoxy]propanoate, in an amount effective to kill said tall fescue or perennial ryegrass but insufficient to damage said turf.

2. The process of claim 1 in which said compound is 4-(4'-chlorophenoxy)-phenoxy-d-propionic-isobutylester.

3. The process of claim 1 in which said compound is methyl 2-[4-(2,4-dichlorophenoxy)-phenoxy]propanoate.

4. The process of claim 1 in which the amount of compound is from 2 to 24 pounds per acre.

5. The process of claim 2 in which the amount of compound is from 8 to 20 pounds per acre.

6. The process of claim 3 in which the amount of compound is from 4 to 12 pounds per acre.

7. A process for the selective control of tall fescue in Kentucky bluegrass, comprising treating said turf with a compound selected from the group consisting of (a) 4-(4'-chlorophenoxy)-phenoxy-d-propionic-isobutylester and (b) methyl 2-[4-(2,4-dichlorophenoxy)-phenoxy]propanoate, in an amount effective to kill said tall fescue but insufficient to damage said Kentucky bluegrass turf.

8. The process of claim 7 in which the amount of compound is from 2 to 24 pounds per acre.